United States Patent [19]

Keggenhoff et al.

[11] Patent Number: 4,774,357

[45] Date of Patent: Sep. 27, 1988

[54] PROCESS FOR PURIFYING POLYISOCYANATES AND THE POLYISOCYANATES THUS PURIFIED

[75] Inventors: Berthold Keggenhoff, Krefeld; Franz-Moritz Richter, Dormagen; Günther Ellendt; Marcel Petinaux, both of Krefeld, all of Fed. Rep. of Germany

[73] Assignee: Bayer Aktiengesellschaft, Leverkusen, Fed. Rep. of Germany

[21] Appl. No.: 638,008

[22] Filed: Aug. 6, 1984

[30] Foreign Application Priority Data

Aug. 11, 1983 [DE] Fed. Rep. of Germany ....... 3329124

[51] Int. Cl.[4] ............................................ C07C 143/00
[52] U.S. Cl. .................................................... 560/352
[58] Field of Search .................... 260/453 SP; 560/352

[56] References Cited

U.S. PATENT DOCUMENTS

| | | | |
|---|---|---|---|
| 3,144,474 | 8/1964 | Kantyka et al. ................... | 260/453 |
| 3,479,384 | 11/1969 | Heiss ................................. | 260/453 |
| 3,816,496 | 6/1974 | Schnabel ...................... | 260/453 SP |
| 3,987,075 | 10/1978 | Schnabel ...................... | 260/453 SP |

Primary Examiner—Alan Siegel
Attorney, Agent, or Firm—Gene Harsh; Joseph C. Gil; Lyndanne M. Whalen

[57] ABSTRACT

Crude polyisocyanates are purified by extraction at a temperature from 80° to 180° C. to form a two-phase system. The phases are separated and the phase made up of purified polyisocyanate and solvent is cooled to a temperature which is at least 50° C. below the extraction temperature. Upon cooling, a second two-phase system forms. Purified polyisocyanate containing residual solvent is recovered upon separation of these phases. Solvent in which polyisocyanate is present that is reclaimed during this process may be reused in subsequent extractions. The purified polyisocyanates have a viscosity which is lower than that of crude polyisocyanates having substantially the same isocyanate content and average functionality. These purified polyisocyanates are useful in the production of polyurethane foams and moldings as well as adhesives and coatings.

9 Claims, 1 Drawing Sheet

PROCESS FOR PURIFYING POLYISOCYANATES AND THE POLYISOCYANATES THUS PURIFIED

BACKGROUND OF THE INVENTION

This invention relates to a process for purifying crude polyisocyanates.

It is known from the literature that crude isocyanate mixtures can be purified by extraction. For example, U.S. Pat. No. 3,144,474 describes a process for purifying isocyanates in which an aliphatic hydrocarbon mixture is added to a 30 to 60% solution of crude isocyanate in chlorinated aromatic hydrocarbons to precipitate out the secondary products. The purified isocyanate is recovered from the solvent mixture by distillation.

German Offenlegungsschrift No. 25 32 722 describes a process for purifying 4,4'-diphenyl methane diisocyanate (MDI). In this disclosed process, a crude mixture which contains at least 80% of 4,4'-MDI in addition to other isomers and up to 5% by weight of relatively high molecular weight fractions obtained by distillation of the isocyanate mixture obtained by the phosgenation of aniline-formaldehyde condensates is used as the starting material. Secondary products and isomers are separated from the mixture by dissolution in hydrocarbons at temperatures of up to 80° C., followed by cooling. The 4,4'-MDI is obtained as end product from the hydrocarbon solution by rectification or crystallization.

German Offenlegungsschrift No. 15 43 258 describes a process for purifying crude polyisocyanates by selective extraction with two solvents of which one is a solvent and the other nonsolvent for the isocyanate mixture, in certain quantitative ratios. The purified polyisocyanate obtained as extract must be separated by distillation from the extractants.

One feature common to each of these processes is that the purified isocyanate is obtained in the form of a solution having a concentration of, in general, only 5 to 20% due to the quantity of extractant required. The solvent must be distilled off at considerable cost in terms of energy to recover solvent-free isocyanate useful for technical applications. In addition, this working up by distillation involves thermal stressing of the isocyanate which may result in the formation of secondary products.

SUMMARY OF THE INVENTION

It has now surprisingly been found that the above-described disadvantages of the prior art can be overcome by carrying out the extraction of crude isocyanates with selected solvents at elevated temperature and subsequently cooling the extract after separation of the impurities. Upon cooling, the purified isocyanate separates as an integral phase and can be recovered by simple phase separation. The solvent phase can be reused for extraction without further purification. Even though undistilled extractant is used, a very effective separation of secondary products is obtained.

BRIEF DESCRIPTION OF THE DRAWING

The drawing is a schematic representation of one apparatus suitable for carrying out the process of the present invention.

DETAILED DESCRIPTION OF THE INVENTION

Figure 1:
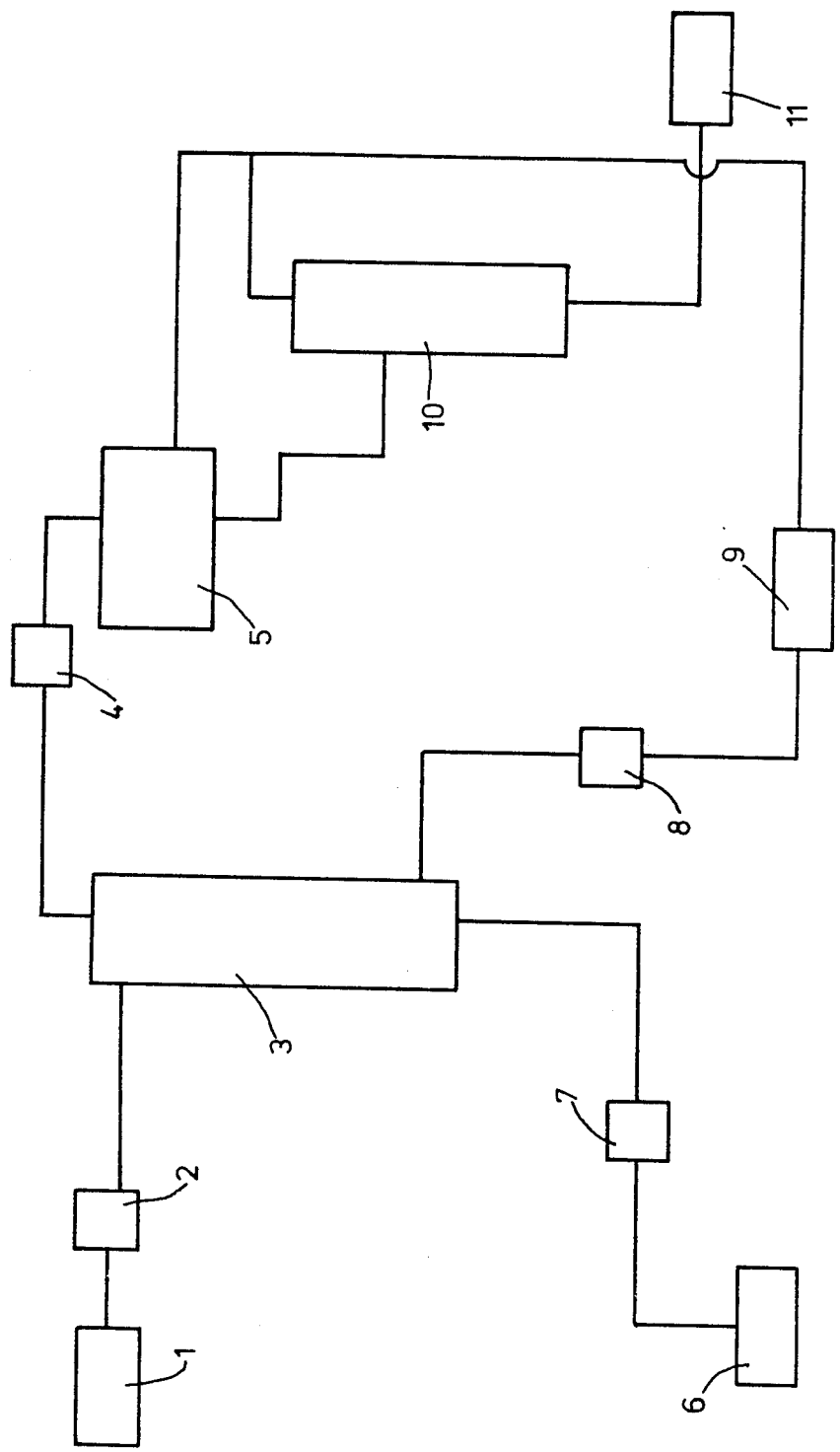

The present invention relates to a process for purifying crude polyisocyanates obtained by phosgenation of the polyamines on which they are based by extraction. More specifically, the polyisocyanate to be purified is extracted at 80° to 180° C. with an extractant in a ratio by volume of extractant to polyisocyanate kept at at least 5:1. The extractant used is a solvent which contains purified polyisocyanate of the type corresponding to the polyisocyanate to be purified in dissolved form. This solvent is only miscible to a limited extent with the polyisocyanate to be purified at temperatures from 80° to 180° C. A two-phase system made up of a main phase and a secondary phase in a ratio by volume of at least 20:1 is formed during the extraction. The main phase is made up of most of the solvent and purified polyisocyanate. This main phase is separated from the secondary phase which contains relatively high molecular weight constituents and impurities of the polyisocyanate to be purified in addition to small quantities of solvent. The main phase is then cooled to a temperature at least 50° C. below the extraction temperature to form a second two-phase system. The lower phase of this second system which is made up of purified polyisocyanate and residues of solvent, is separated from the upper phase which is made up of most of the solvent saturated with purified polyisocyanate. The solvent phase saturated with purified polyisocyanate is preferably reused for extraction, optionally after the addition of more solvent as extractant. The present invention also relates to the polyisocyanates purified by this process.

The process of the present invention may be carried out, for example, in the installation diagrammatically illustrated in the accompanying drawing. In this drawing, the reference numerals have the following meanings:

(1) a storage vessel for the crude polyisocyanate to be purified;
(2) a heat exchanger (heater) for heating the crude polyisocyanate to the extraction temperature;
(3) a countercurrent extraction column;
(4) a heat exchanger (condenser) for cooling the solution of the purified polyisocyanate;
(5) a separator for separating the solvent phase from the product phase (purified polyisocyanate);
(6) a receiver for the enriched secondary phase containing impurities;
(7) a heat exchanger (condenser) for cooling the secondary phase leaving the extractor;
(8) a heat exchanger (heater) for the extractant to be introduced into the extractor;
(9) a storage tank for extractant;
(10) a distillation apparatus for separating residual solvent from the purified polyisocyanate; and
(11) a storage tank for purified polyisocyanate.

The installation diagrammatically illustrated in the accompanying drawing is suitable for carrying out the process of the present invention. This particular installation is not, however, required to carry out the process of the present invention. There are some process steps which, in principle, are not crucial to the invention. For example, separation of the residual solvent from the purified polyisocyanate in a distillation apparatus 10 is only necessary in cases where it is intended to obtain solvent-free polyisocyanate. In addition, it is of course possible to carry out crucial steps of the process according to the invention in apparatus other than those illustrated in the drawing. Thus, for example, the extraction step and the following phase separation step may also be carried out in a battery of mixer-separator units arranged one behind the other or in several extraction columns arranged one behind the other.

Starting materials for the process of the present invention are crude polyisocyanates of the type obtained in the industrial phosgenation of the polyamines on which they are based. Examples of such polyisocyanates are hexamethylene diisocyanate: 1-isocyanato-3,3,5-trimethyl-5-isocyanatomethyl cyclohexane; 2,4- and/or 2,6-diisocyanatotoluene; and polyisocyanate mixtures of the diphenyl methane series of the type obtained by the phosgenation of aniline/formaldehyde condensates on an industrial scale and which are essentially mixtures of from 30 to 90 wt % (based on the mixture as a whole) of diisocyanato-diphenyl methane isomers (particularly 4,4'-diisocyanato-diphenyl methane) with higher homologs. Mixtures of polyisocyanates of the diphenyl methane series are the preferred crude polyisocyanates to be purified by the process of the present invention. In contrast to the commercial diisocyanates, these mixtures of polyisocyanates of the diphenyl methane series cannot be freed from relatively high molecular weight, resin-like constituents, substantially involatile chlorine- or iron-containing compounds and other, often deeply colored impurities by distillation because, in general, only binuclear or, at best, trinuclear components of the polyisocyanate mixtures (not their higher nuclear components) can be distilled without decomposing. Accordingly, it is advisable, particularly with the polyisocyanate mixtures of the diphenyl methane series, to use purification processes instead of or in addition to the other distillationbased purification processes normally used.

It is also possible to use polyisocyanate mixtures of the diphenyl methane series from which a certain quantity of binuclear diisocyanates and, optionally, trinuclear triisocyanates were initially distilled off after phosgenation in the process of the present invention. The resulting distillation residues having a reduced content of di- and, optionally, triisocyanate may then be subjected to the purification process of the present invention.

Before the process of the present invention is carried out, it is important to ensure that the crude polyisocyanates used have a maximum strong solvent content of 10 wt % (based on the mixture as a whole) especially where the solvent is of the type normally used for phosgenation such as chlorobenzene and/or dichlorobenzene. A higher content of solvents such as these would eliminate the miscibility gap between extractant and polyisocyanate to be purified which is crucial to the invention. The polyisocyanates to be purified preferably contain less than 0.5 wt % (based on the mixture as a whole) of phosgenation solvents.

The extractant used in the process of the present invention is a solution of the pure polyisocyanate to be produced in a solvent which is inert to isocyanate groups which solvent is not indefinitely miscible with the crude polyisocyanate at the extraction temperature of 80° to 180° C. (preferably 100° to 150° C.). In general, the extractant is a solution of the pure isocyanate in the solvent which is saturated or substantially saturated at the lowest temperature of the extractant circuit. While it is possible to use pure solvent as the extractant, purification of the solvent reclaimed during the process of the present invention (for example, by separating off the dissolved polyisocyanate by distillation) would be a superfluous measure. The requirement that the solvent used should not be indefinitely miscible with the polyisocyanate to be purified at the extraction temperature implies that there must be a miscibility gap between the two liquids at the extraction temperature. Where such miscibility gap exists and the other parameters of the process (particularly the quantitative ratio of extractant to polyisocyanate) are observed, a two-phase system made up of a main phase and a secondary phase in a ratio by volume of at least 20:1 and up to more than 1000:1 is formed during extraction.

Suitable solvents include aliphatic hydrocarbon solvents which boil above 90° C. under normal pressure, preferably those which have a boiling point under normal pressure in the range from 95° to 320° C. or which have a boiling range of any magnitude within that temperature range. Appropriate hydrocarbons are saturated aliphatic hydrocarbons containing from 8 to 18 carbon atoms, preferably from 8 to 15 carbon atoms and, more preferably, from 10 to 13 carbon atoms or isomer and/or homolog mixtures thereof. It is possible to use both pure hydrocarbon compounds and also technical mixtures thereof. Both branched and straight-chain paraffins or mixtures of hydrocarbons such as these are suitable for use. The solvent preferably contains at least 90 wt % of aliphatic hydrocarbons such as these. The content of aromatic hydrocarbons in the solvent should be below 10 wt %.

In the practical application of the process of the present invention which is preferably carried out continuously, the extraction of the starting polyisocyanate takes place in a first step in which the quantity of extractant is variable within wide limits. In general, the extractant is used in a quantity of at least 5 parts by volume, preferably in a quantity of from 5 to 30 parts by volume and, more preferably, in a quantity of from 10 to 20 parts by volume per part by volume of starting polyisocyanate. Extraction is generally carried out under normal pressure, although it may also be carried out under excess pressure, for example up to 5 bars, should this be appropriate or even necessary due to the boiling point of the extractant. The extraction temperature is in the range from 80° to 180° C., preferably from 100° to 150° C.

In principle, any apparatus known to those skilled in the art may be used for carrying out the extraction process. Extraction is preferably carried out in the form of countercurrent extraction using, for example, combined mixer-separators or countercurrent extraction columns made up of fixed or moving baffles.

During the extraction process, the crude polyisocyanate is dispersed in the heated solvent and is largely dissolved therein to form the "main phase". The impurities and relatively high molecular weight constituents to be removed separate out with very small quantities of the solvent (up to 5 wt % of the solvent used) and form the "secondary phase". The quantity of secondary phase is essentially determined by the extraction temperature, the phase ratio and the number of extraction steps, and the secondary product content of the isocyanate used and, accordingly, may be varied within wide limits. However, since the object of the process is to separate off only the secondary products, the quantity of secondary phase is preferably adjusted by coordinating these parameters to between 1 and 25% by weight and, more preferably, to between 5 and 15% by weight of the starting product (starting polyisocyanate to be purified).

In a second reaction step, the secondary phase is separated from the main phase and optionally worked up separately. In the preferred embodiment of the process where extraction is carried out in the form of countercurrent extraction, the second process step (phase separation) is of course carried out at the same time as the first process step, so that the main phase and secondary phase directly accumulate as separate phases.

The main phase is cooled to a temperature at least 50° C. (generally 50° to 150° C.) below the extraction temperature, preferably in suitable heat exchangers or, optionally, even by evaporation cooling under reduced pressure. During this cooling process, a two-phase mixture is formed from the main phase which two-phase mixture is homogeneous at the elevated extraction temperature. This two-phase mixture is separated in a phase separator. The phases formed upon cooling are (1) a saturated solution of purified polyisocyanate in the major quantity of the solvent present in the original "main phase" and (2) purified polyisocyanate which still contains small residues of solvent (generally about 1 to 20 wt %, based on the mixture of purified polyisocyanate and residual solvent). The solvent residue in phase (2) is generally separated off from the purified polyisocyanate by distillation. In addition to the solvent, this distillate which may also contain a certain amount of diisocyanate is combined with the solvent phase (1) which generally forms the upper phase in the two-phase mixture formed upon cooling. This solvent phase (1) optionally combined with the residual solvent is reheated to the extraction temperature, optionally after intermediate storage, and returned as extractant to the beginning of the process. The purified polyisocyanate preferably freed by distillation from the residual solvent corresponds to the quantity of crude polyisocyanate used, reduced by the quantity separated off with the "secondary phase". The purified polyisocyanate amounts preferably to between 75 and 99 wt % and, more preferably, to between 85 and 95 wt % of the quantity of crude polyisocyanate used.

In one preferred embodiment of the invention, cooling of the "main phase" and heating of the extractant to be returned to the beginning of the process take place in a countercurrent heat exchanger, so that the energy consumption of the process (which is already low) can be further reduced.

If the starting polyisocyanate used contains residues of solvents of the type used for phosgenation such as chlorinated aromatic hydrocarbons, these residues remain partly in the "main phase" and must be removed therefrom. This removal is best done before and/or during cooling of the "main phase", for example by expansion thereof in vacuo, so that the main phase is cooled and the chlorinated aromatic hydrocarbons distilled off in one and the same step.

The process of the present invention is particularly suitable for purifying technical polyisocyanate mixtures of the diphenyl methane series ("MDI polymer types") of the type described above. The MDI-polymer types purified in accordance with the invention show distinctly reduced viscosity by comparison with the crude starting polyisocyanate having substantially the same diisocyanate content and average functionality. If a certain proportion of diisocyanate is distilled off, the products obtained correspond to the starting product in viscosity, but have a considerably higher NCO-functionality. The chlorine contents of the polyisocyanates purified in accordance with the invention are distinctly reduced and the trace contents of iron, which can have a marked effect upon the reactivity of the polyisocyanates are drastically reduced.

Another significant advantage of the MDI-polymer types purified in accordance with the invention lies in their considerably improved color. Whereas the unpurified crude phosgenation products are black liquids, the corresponding polyisocyanate mixtures purified in accordance with the invention are transparent liquids pale yellowish in color.

The polyisocyanates purified in accordance with the invention are suitable for the production of polyurethane foams or even for the production of solid moldings and, by virtue of their faint natural color, may be used for the production of polyurethane-based adhesives and coatings.

The process according to the invention is illustrated but in no way limited by the following example. All parts and percentages are by weight unless otherwise specified.

EXAMPLE 1

In a test apparatus corresponding to that illustrated in the drawing, a stream of 1 kg/h of the starting material was run continuously from receiver 1 for crude, solvent-free MDI-polymer (for analytical data, see below) through the heater 2 into the upper part of a sieve plate extraction column 3 having a length of 180 cm, an internal diameter of 5 cm and a sieve plate interval of 5 cm. In the heater 2, the starting material was heated to 105° C. At the same time, a stream of 20 kg/h of extractant was run from the receiver 9 through the heater 8 into the lower part of the extraction column. The extractant was also heated to 105° C. in the heater 8. The extractant was a solution, substantially saturated at 22° C., of purified polyisocyanate corresponding to the starting polyisocyanate in a solvent which was a technical mixture of $C_{10}$–$C_{13}$ n-paraffins having a boiling range under normal pressure of 190° to 250° C. The starting polyisocyanate and the extractant were passed through the extraction column in countercurrent to one another. The "main phase" accumulating (20.89 kg/h) was cooled in the condenser 4 and the two-phase mixture formed was separated in the separator 5. 95 wt % of the lower phase formed (0.94 kg/h) was purified polyisocyanate and 5 wt % was solvent. This lower phase passed into the distillation stage 10 which was operated at 240° C./10 mbar in the sump. After separation of the residual solvent (0.05 kg/h), the purified polyisocyanate accumulated as the sump product of the distillation stage 10 in a quantity of 0.89 kg/h and was collected in the receiver 11.

The solvent (19.95 kg/h) which accumulated as the upper phase of the separator 5 and which was saturated with purified polyisocyanate at 22° C. was combined with the solvent (0.05 kg/h) accumulated as head product of the distillation stage 10 and passed into the receiver for extractant 9.

92 wt % of the "secondary phase" (0.12 kg/h) accumulated in the sump of the extraction column 3 was separated impurities and relatively high molecular weight constitutents of the starting polyisocyanate and 8 wt % was solvent. After cooling to room temperature in the condenser 7 the secondary phase was collected in the receiver 6.

The starting product and the product purified in accordance with the invention were characterized as follows:

|  | Starting Product | Purified Product |
| --- | --- | --- |
| % Diisocyanate (as determined by gel chromatography) | 41.2 | 41.3 |
| % NCO (MW 42) | 31.25 | 31.7 |
| Viscosity (mPas) | 202 | 86 |
| Chlorine content (%) | 0.29 | 0.20 |
| Iron content (ppm) | 11 | 0.5 |
| Absorbance of a 5% solution in chlorobenzene at 430 nm | 1.19 | 0.168 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for purifying crude polyisocyanate obtained by phosgenation of the polyamine on which the polyisocyanate is based comprising:
   (a) extracting the crude polyisocyanate at 80° to 180° C. with a solvent in a ratio by volume of solvent to polyisocyanate of at least 5:1 to form a two-phase system in which the ratio by volume of main phase to secondary phase is at least 20:1,
   (b) separating the main phase formed in (a) which contains solvent and purified polyisocyanate from the secondary phase,
   (c) cooling the main phase to a temperature which is at least 50° C. below the extraction temperature to form a two-phase system, and
   (d) separating the lower phase of the system formed in (c) from the upper phase of the system.

2. The process of claim 1 in which the upper phase formed in (c) is solvent saturated with purified polyisocyanate which is reused for extraction.

3. The process of claim 2 in which more solvent is added to the recovered solvent saturated with purified polyisocyanate before being reused for extraction.

4. The process of claim 1 in which the purified polyisocyanate and residual solvent phase separated in (d) is freed from residual solvent by distillation.

5. The process of claim 4 in which the residual solvent recovered by distillation is combined with the solvent saturated with purified polyisocyanate separated in (d) and reused for extraction.

6. The process of claim 5 in which the crude polyisocyanate is a mixture of crude polyisocyanates of the diphenyl methane series containing up to 10 wt %, based on the mixture as a whole, chlorinated aromatic hydrocarbon.

7. The process of claim 1 in which the extractant is an aliphatic hydrocarbon solvent.

8. The process of claim 1 in which the crude polyisocyanate is a mixture of crude polyisocyanates of the diphenyl methane series containing up to 10 wt %, based on the mixture as a whole, chlorinated aromatic hydrocarbon.

9. The process of claim 1 in which (a) and (b) are carried out in a continuously operated extraction column.

* * * * *